United States Patent [19]

Mower et al.

[11] Patent Number: 4,765,341
[45] Date of Patent: Aug. 23, 1988

[54] CARDIAC ELECTRODE WITH ATTACHMENT FIN

[75] Inventors: Morton M. Mower, Lutherville, Md.;
Marlin S. Heilman, Gibsonia, Pa.

[73] Assignee: Mieczyslaw Mirowski, Owings Mills, Md.

[21] Appl. No.: 526,208

[22] Filed: Aug. 25, 1983

Related U.S. Application Data

[63] Continuation of Ser. No. 276,066, Jun. 22, 1981, abandoned.

[51] Int. Cl.⁴ .............................................. A61B 1/00
[52] U.S. Cl. ................................................ 128/785
[58] Field of Search ....................... 128/348, 784, 785;
604/164

[56] References Cited

U.S. PATENT DOCUMENTS

| | | | |
|---|---|---|---|
| 4,166,469 | 9/1979 | Littleford | 128/419 P |
| 4,270,549 | 6/1981 | Heilman | 128/784 |
| 4,306,562 | 12/1981 | Osborne | 604/164 |
| 4,313,448 | 2/1982 | Stokes | 128/785 |

*Primary Examiner*—Max Hindenburg
*Attorney, Agent, or Firm*—Fleit, Jacobson, Cohn & Price

[57] ABSTRACT

An implantable cardiac electrode for use in defibrillation and methods of implanting same. The electrode has a metallic mesh electrode surface surrounded by an insulating material. At the proximal end of the electrode there is defined a fin area designed to facilitate placing and securing the electrode proximate the heart. The electrode may be implanted without major surgery in a number of ways, one of which requires a specialized insertion tool which cooperates with a pocket formed in the electrode.

20 Claims, 7 Drawing Sheets

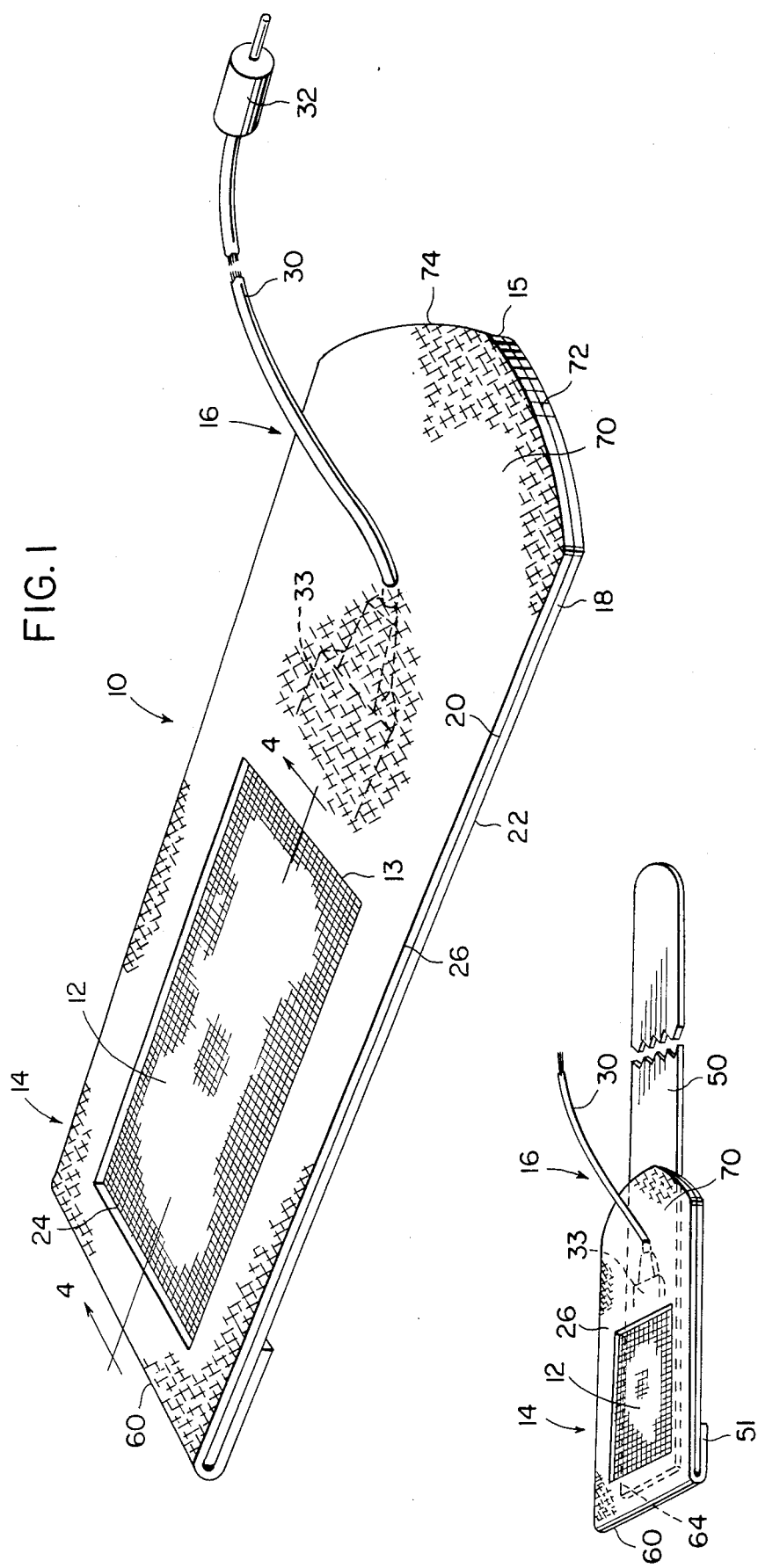

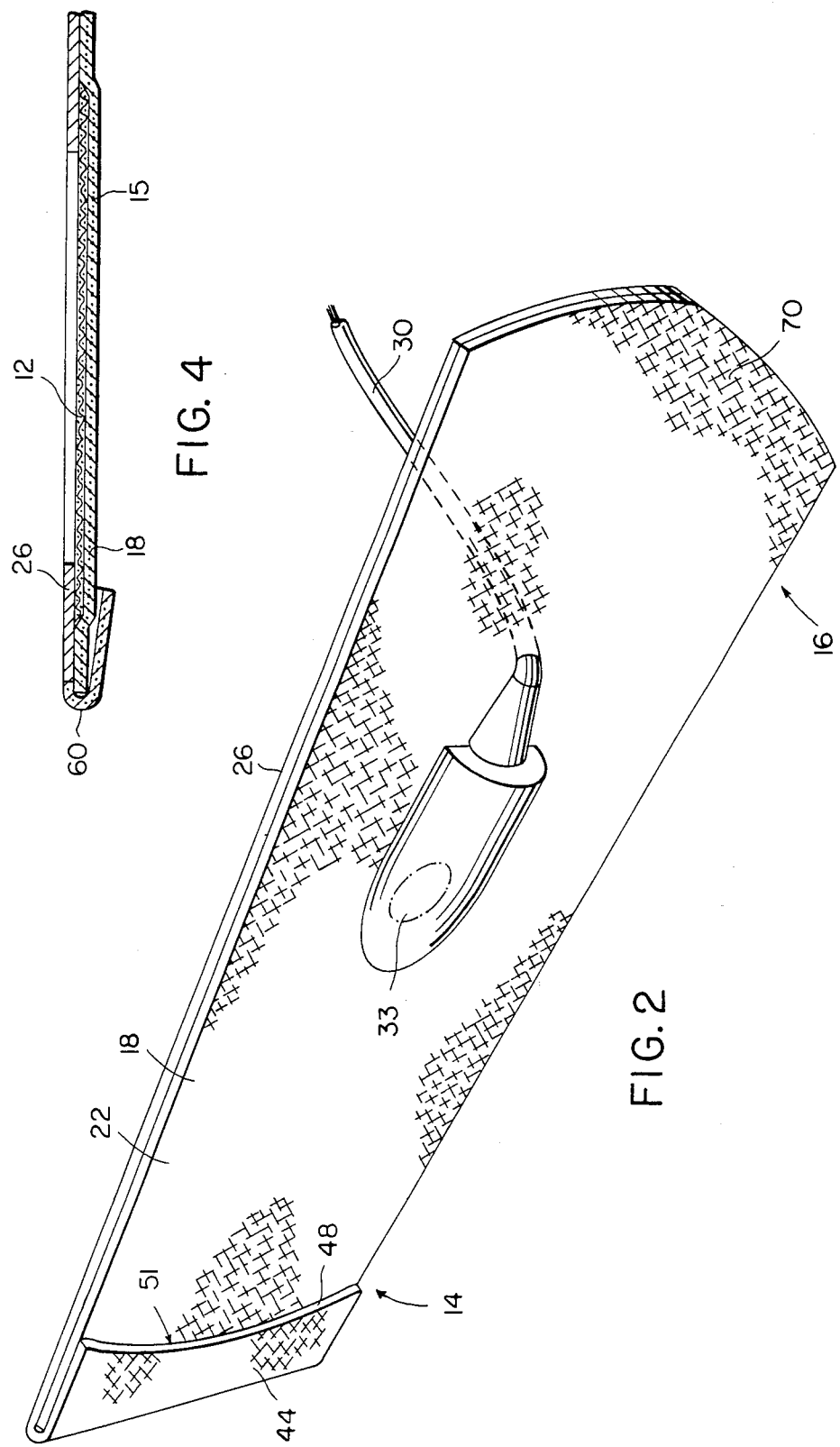

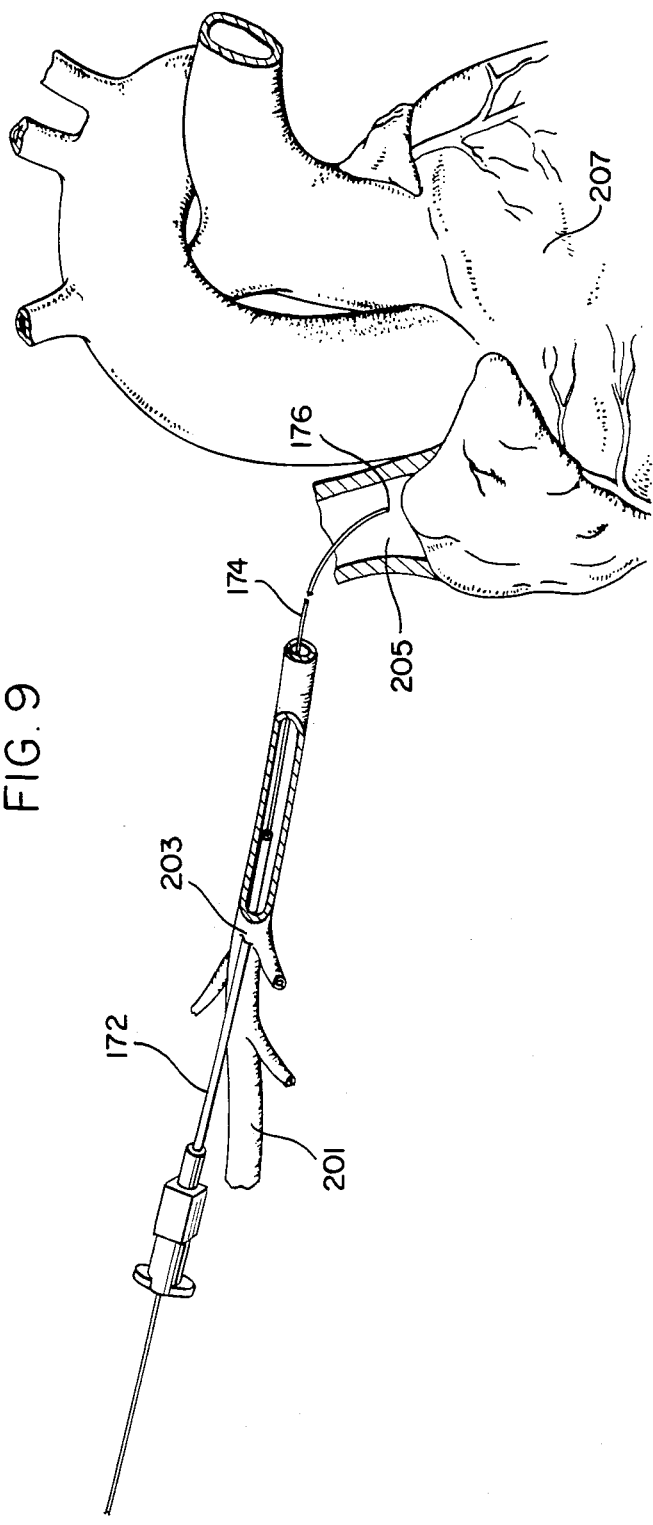
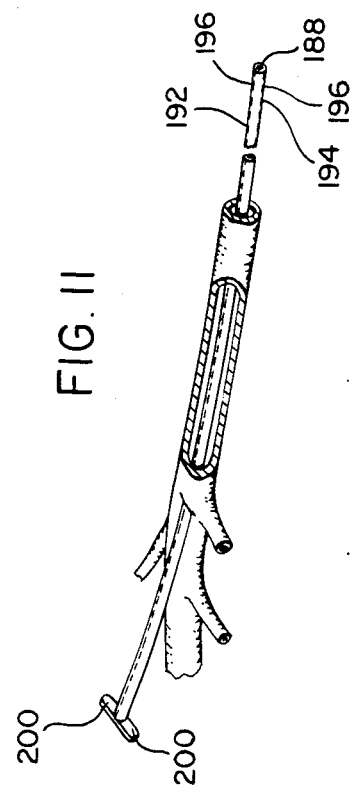
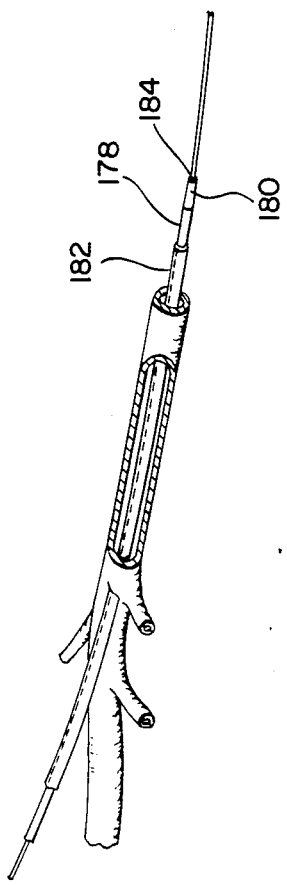

CARDIAC ELECTRODE WITH ATTACHMENT FIN

This application is a continuation of application Ser. No. 276,066, filed June 22, 1981, now abandoned.

BACKGROUND OF THE INVENTION

It is well known that cardiac arrhythmias, such as atrial or ventricular fibrillation, can be overcome by applying electrical energy to the fibrillating myocardium. This procedure, cardioversion or defibrillation, can be accomplished by applying the electrical energy either to the chest of the patient by means of conductive-metal paddles held in place by medical personnel, or during the course of cardiac surgery, by holding conductive-metal paddles in direct contact with the surface of the heart. Such procedures are well known and have been found to be generally effective.

More recently, implantable defibrillators have been proposed for automatically detecting the onset of the cardiac arrhythmia and for automatically correcting such arrhythmia. These automatic defibrillators may employ conformal electrodes, which are maintained in contact with the surface of the heart, or electrodes on an intravascular catheter, or some combination of these. In any case, the electrodes act to impart the desired electrical energy to the heart muscle to achieve difibrillation.

With the intravascular catheter electrode approach, it has been found that, although less electrical energy need be imparted to the heart than in the exterior chest paddles approach, more energy is needed than in the system wherein the electrodes are placed directly in contact with the heart surface. In other words, it has been found that physically placing the electrodes in contact with the exterior of the heart will provide a more efficient use of the electrical energy, thereby reducing the amount of energy required. Obviously, because of a desire to keep the size of the implanted device to a minimum, energy consumption within the device is of the utmost importance.

In the automatic defibrillators previously under consideration, certain of the conformal defibrillation electrodes have been designed for application to the heart by entering the chest cavity and by sewing the electrodes to the heart or positioning the electrodes on the surface of the heart. At times, such electrode implantation may be accomplished during the course of cardiac surgery, such as during a bypass operation. However, even when such heart surgery is not independently required, the earlier surface electrodes required that the chest cavity be opened in order to implant the defibrillating electrodes. This surgical procedure could require intubation of the lungs, and exposes the surfaces of the lungs to possible infection. Additionally, in order for the surgeon to have sufficient working space to effectively position and apply the electrodes, it may be necessary to perform an additional surgical procedure involving spreading two adjacent ribs or splitting the sternum. Accordingly, with these earlier conformal cardiac electrodes, it was necessary to perform major surgery.

Recently, a cardiac electrode has been developed that can be implanted without major surgery. Such an electrode is described in detail in copending U.S. patent application Ser. No. 34,730, entitled "Implantable Cardiac Defibrillating Electrode". Basically, the electrode has a metallic mesh electrode surface surrounded by a protective insulating material. The electrode may be implanted without major surgery by means of an insertion tool which cooperates with a pocket formed in the electrode. After placement of the electrode proximate the heart, the electrode is secured.

Although this new electrode is a significant step forward, there still is room for improvement and a need for a single cardiac defibrillating electrode that can conveniently be positioned and secured proximate hearts of varying sizes without the need for a major surgical procedure. The present invention is directed toward providing that improvement and filling that need.

SUMMARY OF THE INVENTION

The present invention is generally related to the field of electrical defibrillation and, more specifically, to particular cardioverting electrode configurations for use in implantable defibrillators, as well as to methods for the implantation of such electrodes.

"Cardioverting" or "cardioversion" as used herein is intended to encompass the correction of a number of arrhythmic heart conditions, both lethal and nonlethal. Those arrhythmic heart conditions include atrial tachycardia, atrial flutter, atrial fibrillation, junctional rhythms, ventricular tachycardia, ventricular flutter, ventricular fibrillation, and any other non-pacemaking related arrhythmic condition which may be corrected by applying electrical shocks, which are of a magnitude substantially greater than pacing shocks, to the heart. Obviously then "defibrillation" is included in the term cardioversion as a method of applying electrical shocks to the heart to defibrillate fibrillating atria or fibrillating ventricles.

In one embodiment, the cardioverting electrode is of generally elongated rectangular shape and is designed for insertion through the soft tissues outside the pleural cavity for final arrangement proximate or in contact with the heart. The electrode has a specific configuration which provides a flap, or fin, for facilitating placement of the electrode in the desired position relative to the heart.

Basically, the electrode is formed of a metallic mesh or screen which is sandwiched between two layers of a chemically inert, electrical insulation material. The electrode is similar in many respects to the electrode disclosed in the aforementioned U.S. patent application Ser. No. 34,730, which is incorporated by reference herein. Because of its sandwiched construction, the portions of the electrode facing away from the heart, are electrically insulated from the body. The metallic mesh is secured to an electrical lead by a suitable fastening device. Both of the two layers of insulating material extend a predetermined distance beyond the wire lead in a direction away from the forward portion of the electrode (proximally) to define an area which may require sutures or stitches in order to secure the electrode to the soft tissues surrounding the heart, for example, the pericardial sac.

Implantation of the electrode by the inventive method consists of the steps of first making a skin incision on the interior thoracic or abdominal wall, and then positioning the electrode in association with the heart by using, for certain applications, a hand-held instrument to separate the tissue planes and to create a tunnel inside the thorax, but outside the pleural cavity, through the soft tissues surrounding the heart.

Upon creating the tunnel, one or more electrodes may be placed into the tunnel and arranged proximate the surface of the heart. In one embodiment, two electrodes are placed on opposing sides of the heart, inside the pericardium, and means are provided whereby the proximal ends of the electrodes may be sutured to the adjacent pericardial tissue, in order to provide positive electrode fixation. In another manner of practicing the inventive method, a first tunneled space is located between the interior surface of the sternum and the exterior surface of the heart's pericardium, and a second tunnel is created on the heart's inferior surface between the pericardium and the diaphragm.

After the electrodes are arranged proximate the heart, they are secured in place by suturing the fin shaped area of each electrode. The suturing is done as close to the electrode proper as prudent, in a surgical sense, with the remainder of the fin shaped area formed by the two insulating layers, aft of the suturing, being cut away and removed from the surgical site.

In order to perform one preferred version of the method described above, a specialized implantation tool is provided which cooperates with the electrode being implanted to permit relatively easy placement of the electrode in relation to the heart and subsequent withdrawal of the implantation tool. A particular embodiment of the tool is described in the aforementioned U.S. patent application Ser. No. 34,730.

In yet another preferred method, a superior vena cava catheter electrode in combination with a tunneled diaphragmatic electrode is employed. The catheter electrode is inserted using an angiography-like technique, but with a cannula having a pair of opposed weakened areas disposed longitudinally to faciliate removal of the cannula after insertion of the catheter electrode.

It is, therefore, one object of the present invention to provide defibrillating electrodes that are highly efficient in transferring electrical energy to the heart.

Another object of the present invention is to provide defibrillator electrodes that incorporate improved structure for securing the electrodes to the tissue adjacent the heart.

It is a further object of the present invention to provide a defibrillation electrode that may be implanted, arranged and secured in the region of the heart in a manner requiring only a minimum amount of surgery.

Another object of the present invention is to provide a method for implanting and securing a defibrillator electrode adjacent the heart without the need for major surgery.

The manner in which these and other objects are accomplished by the present invention, as well as the many attendant advantages thereof, will become more readily apparent when reference is made to the following description, taken in conjunction with the accompanying drawings.

BRIEF DESCRIPTION OF THE DRAWINGS

FIG. 1 is a top perspective of the inventive electrode;

FIG. 2 is a bottom perspective of the electrode of FIG. 1;

FIG. 3 is a perspective of the electrode of FIG. 1 arranged on an insertion tool prior to implantation of the electrode;

FIG. 4 is a section taken along lines 4—4 of FIG. 1;

FIGS. 9 through 13 are schematic drawings used in explaining the structure associated with and one method of accomplishing the implantation of the catheter electrode. In particular;

FIG. 9 illustrates a needle being inserted into the right innominant vein with a guide wire passing through the needle and terminating at the superior vena cava of the heart;

FIG. 10 illustrates the tubular member with flexible cannula being guided toward the superior vena cava by the guide wire;

FIG. 11 illustrates a portion of the flexible cannula with the tubular member and guide wire removed;

FIG. 12 illustrates the insertion of the catheter electrode into the flexible cannula for implantation of the electrode in the superior vena cava; and FIG. 13 illustrates the catheter electrode in place within the superior vena cava with the flexible cannula being removed from the introduction site in the vein.

DETAILED DESCRIPTION OF THE DRAWINGS

Figure 5:
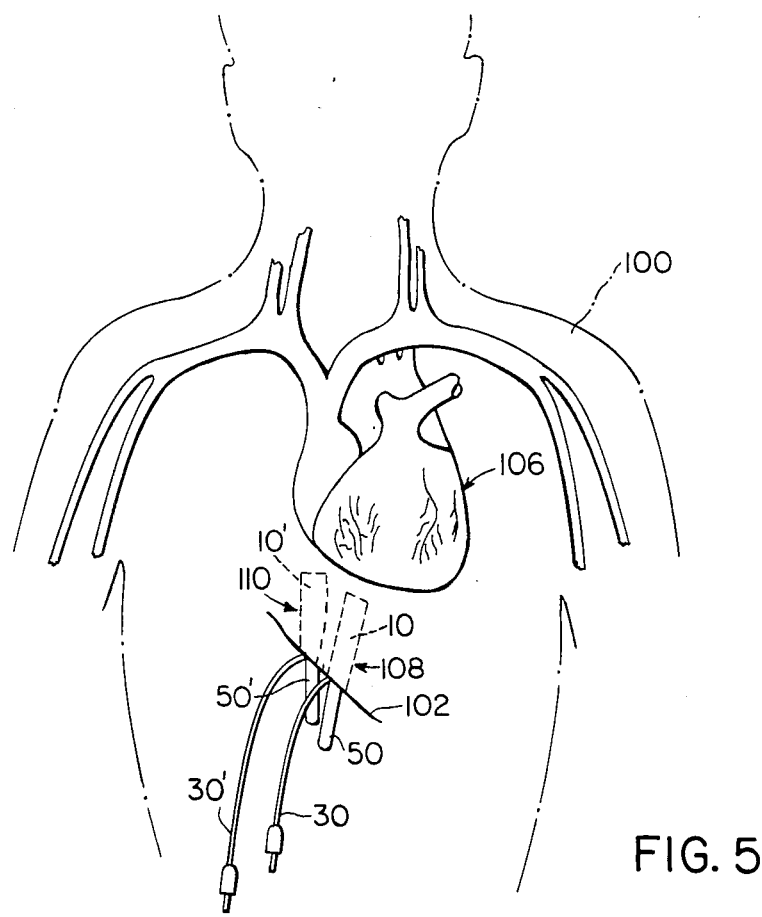
FIGS. 5 and 6 are schematic representations showing one way inserting apical and substernal electrodes into the body with the aid of an insertion tool.

Referring first to FIG. 1, the inventive electrode 10 is formed in a substantially planar, elongated configuration and includes a metallic electrode element formed as a mesh or screen 12, which may be made of titanium or platinum. Alternately, the electrode may be made of expanded platinum. The mesh is a 150 mesh, having 150 elements, or individual wires, per inch. The electrode mesh 12 is first prepared by spot welding together the wires located around the periphery of the mesh. After spot welding, the excess lengths of wires are then ground or machined flush, so as to produce a smooth edge and to form a continuous border.

As oriented in FIG. 1, the electrode 10, which contains a forward body portion 14 and a rearward body portion 16, may be formed of two layers of Silastic with the meatllic electrode element sandwiched therebetween. The electrode 10 is formed by providing a bottom layer 18 having a top surface 20 and a bottom surface 22. The titanium mesh 12 is applied to the top surface 20 of this layer 18, and, a top layer 26 is applied thereon. The thickness of the assembly should be approximately 1 to 3 mm. The top layer 26 has a rectangular aperture 24 cut into it in the forward body portion 14 so that the titanium mesh 12 may make electrical contact with the surface of the heart. In order to provide structural strength, a reinforcing mesh of Dacron may be embedded in both of the Silastic layers and, at the very least, should be used in the bottom layer 18.

Figure 8:
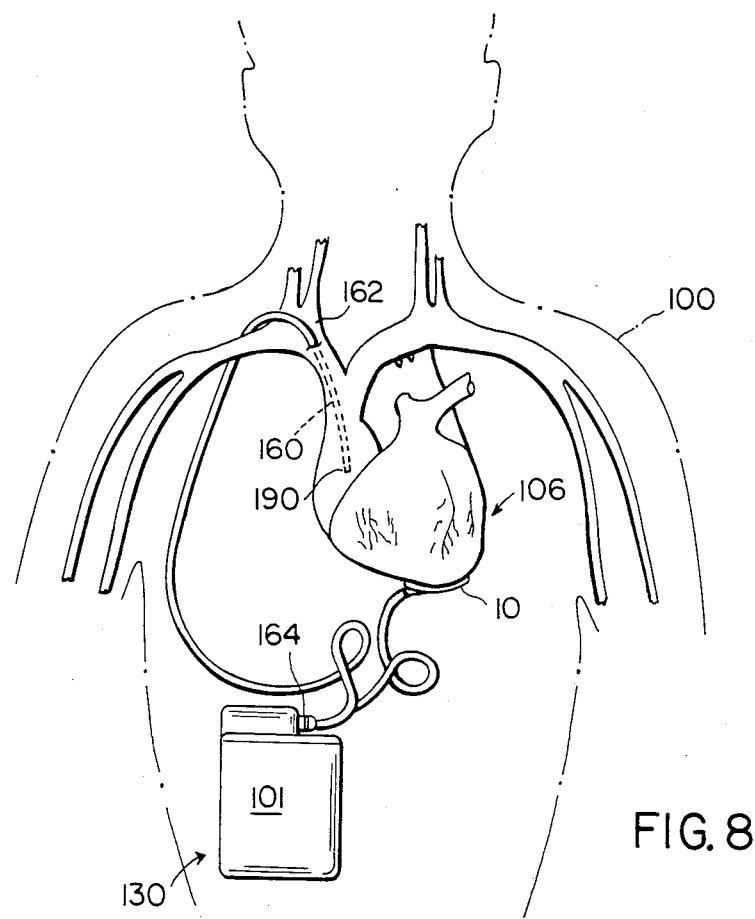
FIG. 8 is a schematic representation showing one way inserting and combining an apical electrode with a catheter electrode.
Figure 12:
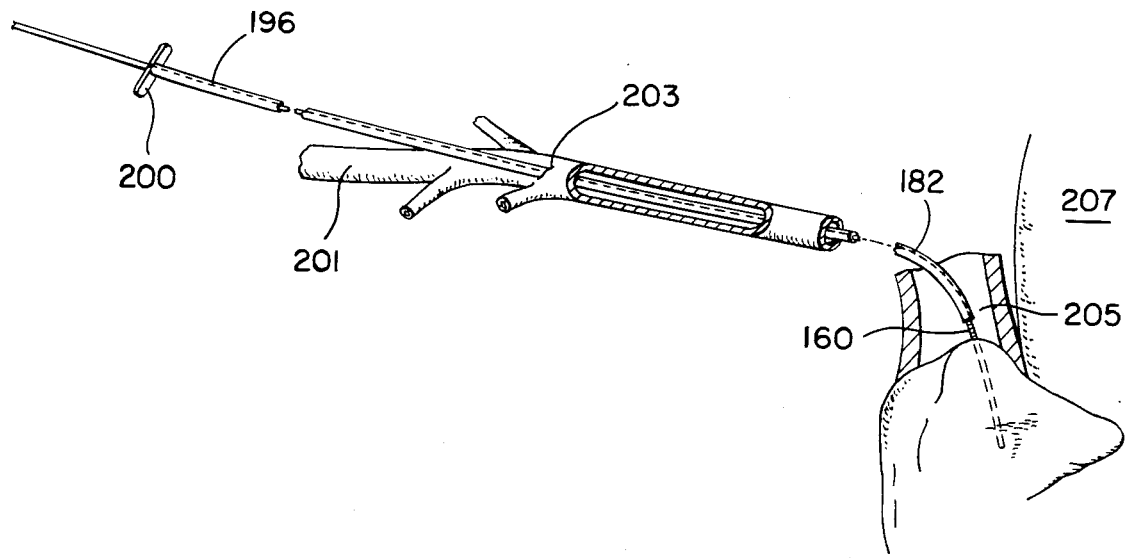

The mesh 12 of the electrode 10 ultimately is connected to the implanted pulse generator 101 of the type shown in FIG. 8 through an insulated cable 30 having a suitable electrical connector 32 located at its proximal end. The other end of the cable 30 is electrically connected to the mesh 12 at a low resistance joint located inside an insulated boot 33.

In the rearward, or proximal, body portion 16 of the electrode, a fin 70 is formed from the two layers 18 and 26. The fin lies in substantially the same plane as that defined in the forward body portion 14 by the Silastic layers.

The fin 70 extends in a proximal direction away from the forward body portion 14 to thus define the rearward body portion 16. The length of the rearward body portion as measured from the rearward edge 13 of the exposed surface of the electrode 12 to the proximal edge 15 of the electrode 10 varies with the intended use of the electrode as either an apical or substernal electrode.

In the case of an apical electrode, the fin extends for a length or distance of from about 4 to about 6 cm., with a distance of about 4 cm. being typical. In the case of a substernal electrode, the fin length is from about 8 to about 12 cm., with a length of about 10 cm. being typical. At its rearwardmost portion, the fin 70 tapers inward toward the longitudinal axis of the electrode 10. This tapering is shown by sides 72 and 74 of the fin. With reference to FIG. 1, it can be seen that the cable 30 is not formed as part of the fin but instead protrudes out of the fin plane very close to where the insulated boot 33 is located.

By employing the attachment fin 70, a universal electrode can be made. Different patients have different size hearts, and this affects the ease of electrode implantation. Therefore, electrodes of different sizes would be a convenience in order to accommodate various heart structures. By providing the attachment fin, however, the surgeon can, based on the size of the heart, tailor the electrode during the surgical procedure by altering the length of the fin structure to precisely fit the needs of the patient and facilitate the surgery. In addition, it is desirable that the electrode remain fairly rigid during insertion, and the provision of the fin area lengthens the electrode body thus increasing its overall stiffness.

As stated above, it is an object of the present invention to provide an energy efficient electrode which does not require creating large incisions or openings in the thorax, in order to effect direct surgical placement of the electrodes. It is also another object of the present invention to construct such electrodes so as to minimize the possibility of any damage to the heart caused when using the electrode for defibrillation.

The two layers 18 and 26 and the metallic mesh 12 may be securely fastened together by placing a silicon rubber adhesive around the periphery of the electrode 10.

The lead 30 is preferably formed of a special, extremely flexible, electric cable, which is particularly suitable for use with implanted cardiac electrodes. Such flexibility is extremely important so as to permit cardiac activity without trauma. One such cable is commonly known as "tinsel" and is formed having a central strand of a polyester yarn and around such central strand are wound six or more conductive strands of silver. Each conductive strand comprises, in turn, its own polyester yarn core and concentrically wound conductive strands. This tinsel wire has an exceedingly long life in the face of mechanical stress, such as flexure. Additionally, since it is formed of silver, the tinsel wire has an extremely low electrical resistance. Another type of cable is that referred to as a "DPS (drawn brazed strand) multifilar conductor", which is a multifilament structural composite formed of nickle-alloy material in a matrix of silver.

Regardless of how it is constructed, the cable 3 must be electrically connected to the titanium mesh 12, and this operation is accomplished on the bottom surface of the mesh by crimping, welding, or some other similar electrical connecting operation or combination of operations. Alternately, the cable 30 may be attached to the mesh 12 by means of a specialized chip which is described in copending U.S. patent application, Ser. No. 34,731, filed Apr. 30, 1979 and entitled "Device and Method for Making Electrical Contact."

Turning now to FIG. 4, the arrangement of the various elements making up the electrode 10 of FIG. 1 is shown in cross section, taken along sight line 4—4 of FIG. 1. In such cross section, the top Silastic layer 26 is bonded to the bottom Silastic layer 18 and the titanium mesh electrode 12 is sandwiched therebetween, all held together by the silicon rubber adhesive.

Also seen in the cross section of FIG. 4 is a layer of Dacron mesh 15 which may be utilized as a strengthening element in either or both Silastic layers of the sandwich. In this embodiment, the mesh 15 is placed in the lower layer 18 and is seen in cross section and at the leading edge 60 of the assembly where stresses occur during implanting. Similar Dacron mesh could also be used to strengthen the top layer 26.

The specialized pouch or pocket arrangement 44 which interacts with the specialized insertion or implantation tool 50, for placement of the electrode 10 with minimum surgical involvement, is shown in cross section also. As can be seen in FIGS. 2 and 3, the pocket or pouch 44 is formed by continuing the top layer 26 of Silastic down over the leading edge 60 of the electrode so as to form a lip 48 which extends parallel to the bottom layer 18 of the electrode, thereby forming a pocket 51 across the entire width of the electrode to receive the insertion tool. Additionally, a portion of Dacron mesh 15 may be embedded in the pocket or pouch 44 in order to provide added strength to the pocket to prevent tearing by the insertion tool.

As described above, it is an object of the present invention to provide a method of implanting a defibrillation electrode system without the need for major chest surgery, by incizing either the interior thoracic or abdominal wall. Hence, by means of a specially provided hand-held instrument, the tissue planes are separated and a tunnel is created inside the thorax but outside the pleural cavity through the soft tissues which surround the heart. After forming a tunnel, one or more electrodes may be inserted into the tunnel and arranged proximate the surface of the heart. The present invention contemplates the forming of one tunnel between the interior surface of the thorax and the exterior surface of the heart's pericardium and either attendantly or in a later step, the insertion of one or more electrodes through such tunnel for ultimate placement proximate the heart. Additionally, the present invention teaches another tunnel created on the diaphragmatic surface of the heart's pericardium, between the pericardium and the diaphragm, and also placement of cardiac electrodes through this second tunnel.

Turning to FIG. 5, the silhouette of the thoracic region of a patient 100 is shown, and the foregoing incision location is shown at 102. In the silhouette of FIG. 5, the location and general outline of the patient's heart is seen at 106. In regard to the abdominal incision 102, whereat the incision tool 50 may be seen partially protruding through this incision, the tunnel 108 is being created on the inferior surface of the heart's pericardium between the pericardium and the diaphragm. The inventive electrode 10 is shown in position and retained on the insertion tool 50. The lead 30 is also shown protruding from the incision 102.

Referring for a moment to FIG. 3, the electrode 10 is shown installed on the specialized insertion tool 50, with the leading edge 64 of the insertion tool having been inserted into the pocket 51 formed in the back surface of the inventive electrode 10. As may be seen in phantom, the leading hard edge 64 of the insertion tool 50 is at the front of the electrode 10. During insertion through the soft tissue planes, the electrode 10 and the hard leading edge 64 of the insertion tool cooperate to form the tunnel.

Referring back to FIG. 5, it may be seen that a second tunnel 110 is being formed as indicated above for placement of a substantial patch electrode 10'. The tunnel 110 originates at the same incision 102 as tunnel 108 and is created between the interior surface of the thorax and the anterior surface of the heart's pericardium.

Figure 6:
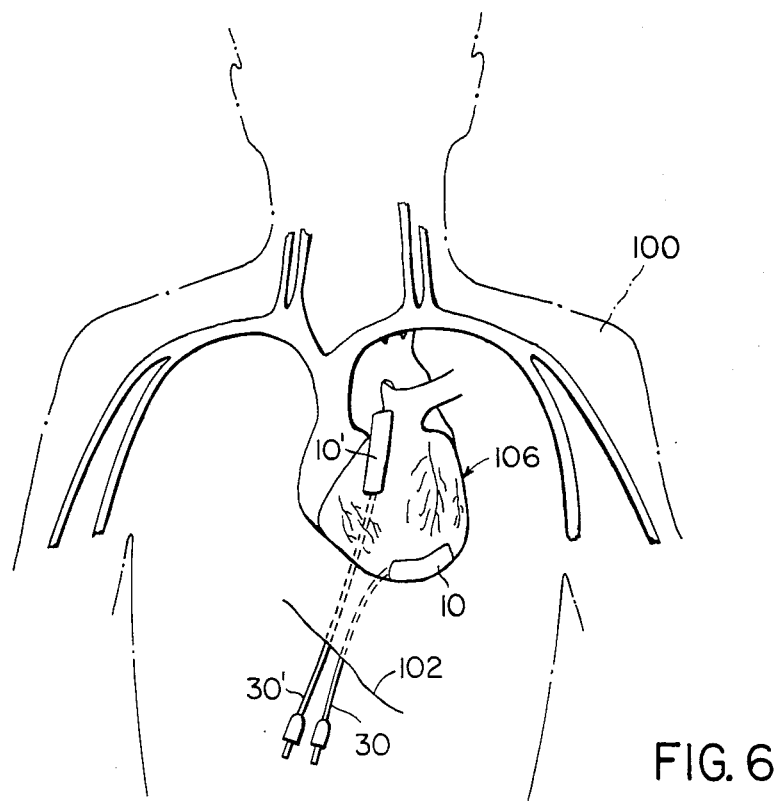

In FIG. 5, it may be seen that, after completely inserting the insertion tool 50, the tunnels 108 and 110 are fully formed, and upon withdrawing the insertion tool, the leading edge portion 64 of the tool slips out of the pocket 51 of the electrode 10 and the electrode remains at its original location. FIG. 6 shows apical electrode 10 and substernal electrode 10' in place after having been inserted through the tunnels formed in the soft tissue planes and after having the insertion tool withdrawn from the tunnels. In FIG. 6, the leads 30 and 30' are shown extending through the incisions. These leads ultimately will be tunneled to the site of and connected to the implanted defibrillator 101 (FIG. 8).

In order to secure the patch to the heart muscle, at least two sutures are preferred. It has been found advantageous to place one on the proximal edge of the electrode and the other on a side edge of the electrode. Thus, the electrode is fixed by two or more spaced-apart sutures on the accessible periphery of the flexible electrode. In this way, the flexible electrode, once fixed proximate the heart, is prevented from rotary motion within the plane of the electrode; however, the electrode is still capable of flexing in and out of the plane in conformance with the movement of the heart itself. In this way, optimum electrical contact between the surfaces of the heart and the open mesh electrode 12 is ensured.

Figure 7:
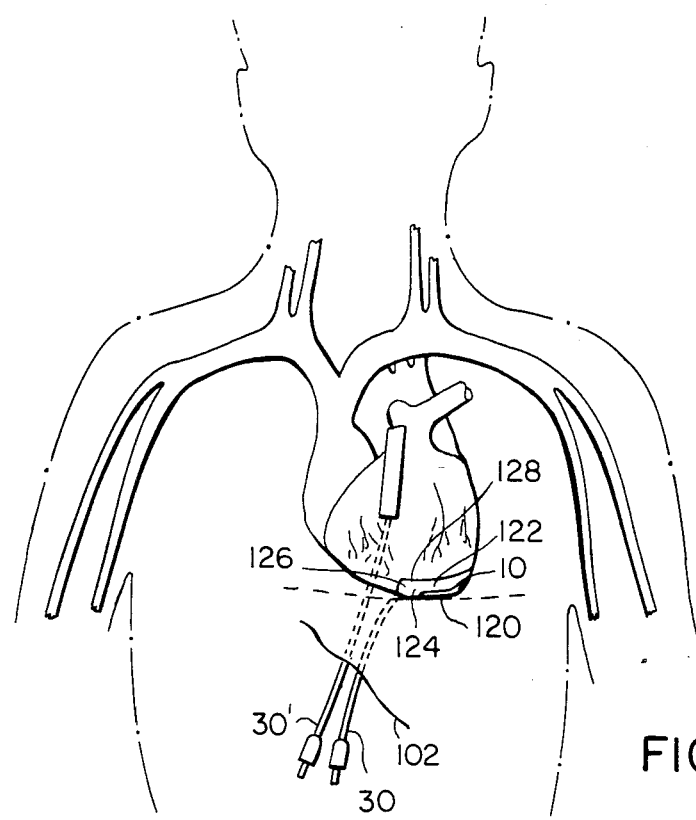
FIG. 7 is a schematic representation used to explain insertion of apical and substernal electrodes without need for the insertion tool.

The electrode 10, because of the strength induced by its elongated construction, may be implanted without the use of a special tool. FIG. 7 illustrates one such method of implanting. As before, an incision 102 is made below the xiphoid. The tissue planes at the incision are then separated to reveal the longitudinal plane 120 (shown in phantom) where the pericardium is attached to the diaphragm.

An inverted "T" incision is made in this longitudinal plane and the apical electrode 10 is inserted so that its planar portion is substantially parallel to the plane 120 with the conductive electrode surface being proximate the heart. Once implanted, the apical electrode is then secured to the pericardium or the pericardium/diaphragm interface by two or more spaced-apart sutures on the accessible periphery of the flexible electrode, for example, at point 122 along edge 124 and at point 126 on the proximal edge 128.

The substernal electrode 10' is implanted in the same manner as previously described with regard to the implantable tool 50. However, because of the strength induced by its elongated construction, the substernal electrode 10' may be moved into position without any need for the tool 50.

There are also other procedures which may be followed in applying the inventive electrodes to the heart. In one such method, a superior vena cava catheter electrode is coupled with a tunneled diaphragmatic electrode.

With reference to FIGS. 8-11, under this procedure, the diaphragmatic electrode 10 is inserted as explained hereinbefore. After incision below the xiphoid, the electrode 10 is inserted between the pericardium and diaphragm, or in the interpericardial space. The proximal end of the electrode (the leads) then is tunneled to a subcutaneous or submuscular pocket 130 for subsequent connection to the implantable cardioverter 101.

After placement of the diaphragmatic electrode has been accomplished, the necessary steps are taken to implant the superior vena cava electrode 160. Briefly stated, after an incision below the clavicle, the catheter electrode enters either the axillary or cephalic vein 162. The catheter electrode is inserted and passed to the superior vena cava or right atrium with fluoroscopic guidance. The proximal end with connectors 164 of the catheter electrode is then tunneled down the left side of the chest to the pulse generator pocket.

Alternatively, the catheter electrode enters the jugular vein and is passed to the superior vena cava or right atrium. In yet another method, the introduction site is the right imnominant vein.

With reference to FIG. 8-13, a preferred method of inserting the superior vena cava catheter electrode 160 may be described. Under this method, a needle 172 of predetermined cross section is inserted into the right imnominant vein 201 at introduction site 203 above the clavicle and punctures the vein in the chest as shown in FIGS. 8 and 9. A guide wire 174 having a diameter less than the internal diameter 104 of the needle is inserted and directed through the needle 172, under fluoroscopic guidance, into the vein and guided so that the end 176 of the guide wire terminates at the superior vena cava 205 or right atrium of the heart 207. The needle is then removed, leaving the guide wire in place.

As shown in FIG. 10, a hollow flexible tubular structure 178 terminates at one end in a tapered point 180. The exterior diameter of the tube is dimensioned so that it may be received within a hollow flexible cannula 182.

The tubular member 178 contains a bore 184 at the pointed end 180, sized to receive the guide wire 174. In this way, the guide wire directs the tubular member with the flexible cannula to the desired location within the vein. When the tubular member and the cannula have been fully inserted so that the cannula has its end 188 at the superior vena cava, first, the guide wire 174 is removed, and then the tubular member 178, thus, leaving the flexible cannula 188 in final position (FIG. 11) for subsequent introduction of the super vena cava catheter electrode 160.

Figure 13:
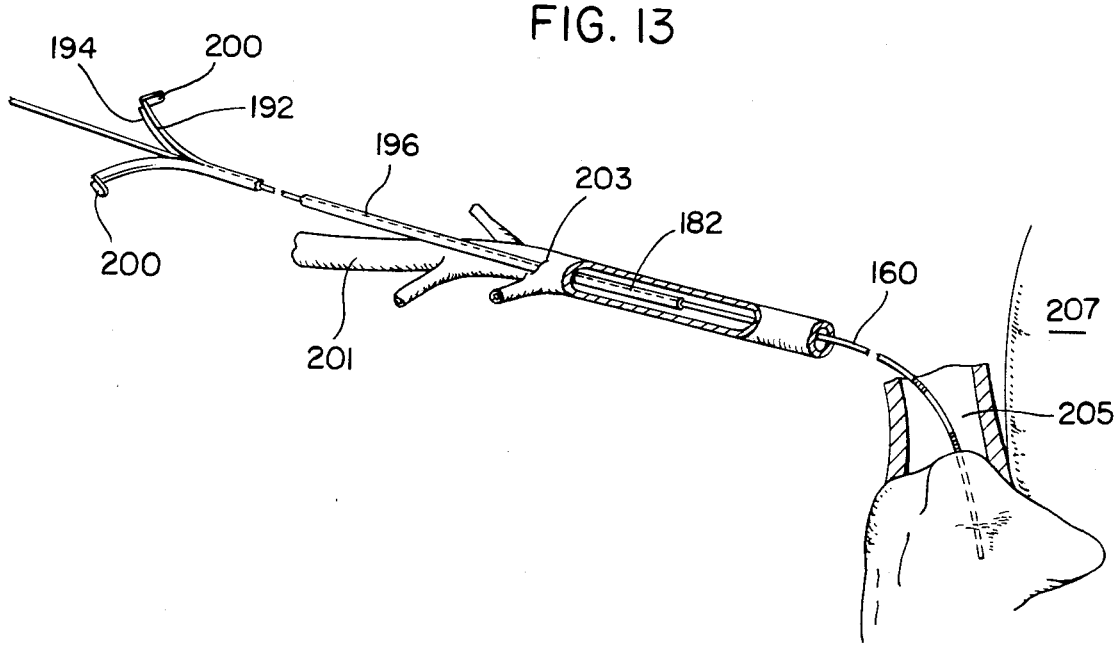

After the catheter electrode 160 has been directed through the flexible cannula with the electrode tip 190 being positioned in the superior vena cava (FIG. 12), the cannula is then removed (FIG. 13). This removal is best accomplished when the cannula contains a pair of opposed weak spots 192 and 194 disposed longitudinally along the substantial length of the cannula. Typically these weak spots are produced by providing a series of closely spaced, longitudinally-disposed tiny perforations 196. The cannula at its proximal end contains a pair of tabs 200. In order to facilitate its removal, the cannula is withdrawn a short distance from the introduction site 203 leaving the electrode 160 undisturbed. The tabs 200 are then grasped and pulled away from each other to cause the cannula to break in two along the weak spots 192 and 194. This procedure is repeated until removal is accomplished.

It is, of course, understood that the above detailed description is intended by way of example only and is not intended to limit the present invention in any way, except as set forth in the following claims.

What is claimed is:

1. An implantable cardioverting electrode assembly for placement proximate the heart and for connection to a suitable cardioverting system, the assembly comprising:
    an elongated planar body divided into forward and rearward portions;
    said forward portion including a flexible electrically conductive planar electrode for placement proximate the heart, said planar body occupying substantially the entire area of said forward portion;
    said rearward portion defining a planar fin adjacent to and occupying the same plane as said planar electrode for providing an electrically insulated area of substantially the same width as the remainder of said planar body for suturing the electrode assembly to tissue adjacent the heart, said fin lengthening said planar body to increase the overall stiffness of said planar body;
    said fin being of sufficient length as measured along the longitudinal axis of said elongated planar body to define an insulated area that may be removed as by cutting by the user to provide a universal planar body of varying length to accommodate hearts of different sizes; and
    electrical conductor means arranged to electrically connect said electrode and said cardioverting system, said electrical conductor means not forming part of said fin.

2. The assembly of claim 1 further comprising an electrical insulating element covering the surface of said planar electrode facing away from the heart.

3. The assembly of claim 2 further comprising a reinforcing mesh embedded in said electrical insulating element to provide added mechanical strength thereto.

4. The assembly of claim 1 wherein said planar electrode is formed of titanium mesh.

5. The asesmbly of claim 1 further comprising a pocket formed in the back surface of said planar body adapted to receive a leading edge of a tool used to implant said electrode assembly.

6. An electrode of the type for implantation in a patient for connection to an electrical cardioverting system, said electrode comprising:
    a planar electrical conductor;
    a first elongated layer of electrical insulating material, said layer being divided approximately in half by a transverse plane that is approximately perpendicular to the plane defined by said first layer to define on said first layer a first portion on one side of said transverse plane and a second portion on said first layer on the other side of said transverse plane, said first portion arranged to coincide with and entirely cover one side of said planar electrical conductor; and
    a second layer of electrical insulating material of substantially the same size as said first layer, said second layer having at least one large aperture therein for exposing the central portion of said conductor, the remainder of said second layer covering a perimeter portion of said conductor and covering said second portion of said first layer, said second portion defining an insulated area free of said planar electrical conductor for suturing the electrode to tissue adjacent the heart, said second portion lengthening said electrode to increase the overall stiffness of said electrode, said second portion being of sufficient length as measured along the longitudinal axis of said elongated first layer to define an area that may be removed as by cutting by the user to provide a universal electrode of varying length to accommodate hearts of different sizes.

7. The electrode of claim 6, further comprising flexible electrical conductor means connected to said planar electrical conductor and the electrical cardioverting system.

8. The electrode of claim 7, wherein said flexible electrical conductor means comprises a lead having one end secured to said planar electrical conductor.

9. The electrode of claim 8, wherein said lead is made from silver tinsel wire.

10. The electrode of claim 8, wherein said lead is made from drawn brazed strand cable.

11. An electrode of the type for implantation in a patient for connection to an electrical cardioverting system, said electrode comprising:
    a planar electrical conductor,
    a first layer of electrical insulating material arranged to coincide with and entirely cover one side of said planar electrical conductor,
    a second layer of electrical insulating material of substantially the same size as said first layer, said second layer having at least one large aperture therein for exposing the central portion of said conductor and covering a perimeter portion of said conductor,
    flexible electrical conductor means connected to said planar electrical conductor and the electrical cardioverting system, said first and second insulating layers forming a planar fin area near said conductor means, said fin area being free of said planar electrical conductor and lying in substantially the same plane as said planar electrical conductor for suturing said electrode to tissue adjacent the heart, said fin area lengthening said electrode to increase the overall stiffness of said electrode, and
    said fin area being of sufficient length as measured along the longitudinal axis of said elongated first layer to define an area that may be removed as by cutting by the user to provide a universal electrode of varying length to accommodate hearts of different sizes.

12. The electrode of claim 11 wherein said planar electrical conductor is formed of titanium mesh.

13. The electrode of claim 11 wherein said planar electrical conductor is formed of an expanded platinum sheet.

14. A method of implanting and securing a cardioverting electrode proximate the human heart, the electrode having a proximal attachment fin, said method comprising the steps of:
    providing a cardioverting elecrode divided into forward and rearward portions, said forward portion including a flexible electrically conductive planar electrode which occupies substantially the entire area of said forward portion, said rearward portion including a planar fin adjacent to and occupying the same plane as the planar electrode for providing an insulated area of substantially the same width as the remainder of the planar electrode, said fin lengthening the cardioverting electrode to increase the overall stiffness of the cardioverting electrode, said fin being of sufficient length as measured along the longitudinal axis of said elongated planar body to define an area that may be removed as by cutting by the user to provide a universal electrode of varying length to accommodate hearts of different sizes;

making a skin incision in the upper abdominal wall, said skin incision terminating at the soft tissue surrounding the heart;

inserting said cardioverting electrode having an electrically conductive area into said incision, and locating said conductive area of said electrode proximate the heart surface;

securing said cardioverting electrode to the soft tissue by using at least two spaced-apart sutures on the accessible rearward portion of the fin of the cardioverting electrode that is spaced from said conductive area; and altering the length of the fin to accommodate the heart to which the cardioverting electrode is secured.

15. The method of claim 14, wherein one of said sutures is on the proximal edge of the electrode and another of said sutures is on a side edge of the electrode.

16. The method of claim 14, wherein said soft tissue is the inferior side of the heart's pericardium between the pericardium and the diaphragm.

17. A method of implanting and securing a cardioverting electrode proximate the human heart, the electrode having a proximal attachment fin, and implanting and securing a cardioverting catheter electrode in the heart, the method comprising the steps of:

providing a cardioverting electrode divided into forward and rearward portions, said forward portion including a flexible electrically conductive planar electrode that occupies substantially the entire area of said forward portion, said rearward portion including a planar fin adjacent to and occupying the same plane as the planar electrode for providing an insulated area of substantially the same width as the remainder of the planar electrode, said fin lengthening the cardioverting electrode to increase the overall stiffness of the cardioverting electrode, said fin being of sufficient length as measured along the longitudinal axis of said elongated planar body to define an area that may be removed as by cutting by the user to provide a universal electrode of varying length to accommodate hearts of different sizes;

making a skin incision in the upper abdominal wall, said skin incision terminating at the soft tissue surrounding the heart;

inserting said cardioverting electrode having an electriclaly conductive area into said incision, and locating said conductive area of said electrode proximate the heart surface;

securing said cardioverting electrode to the soft tissue by using at least two spaced-apart sutures on the accessible rearward portion of the fin of the cardioverting electrode that is spaced from said conductive area;

altering the length of the fin to accommodate the heart to which the cardioverting electrode is secured;

inserting a needle of predetermined cross section into the right innominate vein of the patient;

inserting a guide wire having an external diameter less than the internal diameter of the needle into the needle;

directing the guide wire into the vein until the end of the guide wire reaches the superior vena cava;

removing the needle and leaving the guide wire in place;

causing the guide wire to guide a tubular member contained within a flexible cannula to the superior vena cava;

removing the guide wire, when an end of the flexible cannula is in the superior vena cava;

inserting the catheter electrode into the cannula, the cannula guiding the tip of the catheter electrode to the superior vena cava; and removing the cannula, when the tip of the catheter electrode is in the superior vena cava.

18. The method of claim 17, wherein said cannula has a pair of opposed weak spots disposed longitudinally along the substantial length of the cannula, the proximal end of the cannula having a pair of opposed tabs, and wherein said cannula removing step comprises:

withdrawing the cannula a short distance from the introduction site; and pulling the tabs away from each other to cause the cannula to break into along the weak spots.

19. An implantable cardioverting electrode assembly for placement proximate the heart and for connection to a suitable cardioverting system, the assembly comprising:

an elongated planar body divided into forward and rearward portions;

said forward portion including a flexible electrically conductive planar electrode for placement proximate the heart, said planar electrode occupying substantially the entire area of said forward portion;

said rearward portion defining a planar fin adjacent to and occupying the same plane as said planar electrode for providing an insulated area of substantially the same width as the remainder of said planar body for suturing the electrode asesmbly to tissue adjacent the heart, said fin being of sufficient length as measured along the longitudinal axis of said elongated planar body to define an area that may be removed as by cutting by the user to provide a universal electrode of varying length to accommodate hearts of different sizes, said fin lengthening said planar body to increase the overall stiffness of said planar body, said forward and rearward portions being defined by the same insulating material, said planar electrode being positioned within said insulating material and confined to the forward portion of said body; and electrical conductor means arranged to electrically connect said electrode and said cardioverting system, said planar electrode not forming part of said fin means.

20. An electrode of the type for implantation in a patient for connection to an electrical cardioverting system, said electrode comprising:

a planar electrical conductor;

a first elongated layer of electrical insulating material, said layer being divided approximately in half by a transverse plane that is approximately perpendicular to the plane defined by said first layer to define on said first layer a first portion on one side of said transverse plane and a second portion on said first layer on the other side of said transverse plane, said first portion arranged to coincide with and entirely cover one side of said planar electrical conductor; and a second layer of electrical insulating material of substantially the same size as said first layer, said second layer having at least one large aperture therein for exposing the central portion of said conductor, the remainder of said second layer covering a perimeter portion of said conductor and covering said second portion of said first layer, said planar electrical conductor being disposed between said first and second layers in the area of said first portion, said second portion defining an insulated area free of said planar electrical conductor for suturing the electrode to tissue adjacent the heart, said second portion lengthening said electrode to increase the overall stiffness of said electrode, said second portion being of sufficient length as measured along the longitudinal axis of said elongated first layer to define an area that may be removed as by cutting by the user to provide a universal elecrode of varying length to accommodate hearts of different sizes.

* * * * *